United States Patent
Webster et al.

(10) Patent No.: US 6,583,171 B1
(45) Date of Patent: Jun. 24, 2003

(54) ANTINEOPLASTIC AGENTS

(75) Inventors: John Malcolm Webster, North Vancouver (CA); Jianxiong Li, Port Moody (CA); Genhui Chen, Burnaby (CA)

(73) Assignee: Welichem Biotech Inc., Burnaby (CA)

( * ) Notice: Subject to any disclaimer, the term of this patent is extended or adjusted under 35 U.S.C. 154(b) by 0 days.

(21) Appl. No.: 09/519,871

(22) Filed: Mar. 6, 2000

Related U.S. Application Data (63) Continuation of application No. PCT/CA98/00841, filed on Sep. 3, 1998, which is a continuation of application No. 08/921,851, filed on Sep. 2, 1997, now abandoned, which is a continuation of application No. 08/627,589, filed on Apr. 4, 1996, now abandoned.

(51) Int. Cl.⁷ .............................................. A61K 31/40
(52) U.S. Cl. ...................................... 514/421; 548/453
(58) Field of Search ........................... 548/453; 514/421

(56) References Cited

U.S. PATENT DOCUMENTS

| | | | | |
|---|---|---|---|---|
| 4,672,130 A | * | 6/1987 | Rhodes et al. | 548/453 |
| 4,760,077 A | * | 7/1988 | Stahl et al. | 514/412 |
| 5,292,892 A | | 3/1994 | Takahashi et al. | 548/453 |
| 5,399,711 A | * | 3/1995 | Takahashi et al. | 548/453 |
| 5,827,872 A | * | 10/1998 | Webster et al. | 514/421 |
| 6,020,360 A | * | 2/2000 | Webster et al. | 514/421 |
| 6,316,476 B1 | * | 11/2001 | Webster et al. | 514/360 |

FOREIGN PATENT DOCUMENTS

| | | |
|---|---|---|
| WO | WO 84/01775 | 5/1984 |
| WO | WO 94/26750 | 11/1994 |
| WO | WO 94/28001 | 12/1994 |
| WO | WO 96/23795 | 8/1996 |
| WO | WO 96/32396 | 10/1996 |

OTHER PUBLICATIONS

Eisenman, et al., Antibiotics and Chemotherapy, *A New Sulfur–Containing Antibiotic, Produced by a Streptomyces, Active Against Bacteria and Fungi, Antibiotics and Chemotherapy* 3(4):385–392 (1953) (copy enclosed).

Celmer, Walter D., et al., Structure of Thiolutin and Aureothricin, *The Structures of Thiolutin and Aureothricin, Antibiotics Containing a Unique Pyrrolinonodithiole Nucleus, Structure of Thiolutin and Aureothricin,* 77:2861–2865 (May 20, 1955) (copy enclosed).

von Daehne et al., "New Antibiotics Containing the 1,2–dithiolo(4,3–b)pyrrole Ring System," *J. Antibiotics* 22:233–235 (May, 1969).

Jimenez et al., "Mode of Action of Thiolutin, and Inhibitor of Macromolecular Synthesis in Saccharomyces cerevisiae," *Antimicrobial Ag. Chemother.*, 3(6):729–738 (Jun., 1973) (copy enclosed).

Tipper et al., "Inhibition of Yeast Ribonucleic Acid Polymerases by Thiolution," *J. Bacteriol.* 116:245–256 (1973).

Hagio et al., "Total Synthesis of Holomycin, Thiolutin, and Aureothricin," *Bull. Chem. Soc. Japan,* 47:1484–1489 (1974).

Ninomiya et al., "Biochemically Active Substances from Microorganisms. V.1) Pyrrothines, Potent Platelet Aggregation Inhibitors of Microbial Origin," *Chem. Pharm. Bull.*, 28:3157–3162 (Nov. 1980) (copy enclosed).

Shroeder et al., "Synthesis and Biological Effects of acyclic Pyrimidine Nucleoside Analogues," *J. Med. Chem.* 24:1078–1083 (1981).

Bergeron et al., "Antineoplastic and Antiherpetic Activity of Spermidine Catecholamide Iron Chelators," *Biochem. Bioph. Res. Comm.* 121:845–854 (1984).

Akhurst et al., "A Numerical Taxonomic Study of the Genus Xenorhabdus (Enterobacteriaceae) and Proposed Elevation of the Subspecies of X. nematophilus to Species," *J. Gen. Microbiol.* 134:1835–1845 (1988) (copy enclosed).

Skehan et al., "New Colorimetric Cytotoxicity Assay for Anticancer–Drug Screen," *J. Natl. Cancer Inst.* 82:1107–1118 (1990).

Mehta et al., "Characterization of Effective Chemopreventive Agents in Mammary Gland in Vitro Using an Initiation–Promotion Protocol," *Anticancer Res.* 11:593–596 (1991) (copy enclosed).

Monks et al., "Feasibility of a High–Flux Anticancer Drug Screen Using a Diverse Panel of Cultured Human Tumor Cell Lines," *J. Natl. Cancer Inst.* 83:757–766 (Jun. 5, 1991) (copy enclosed).

McInerney et al., "Biologicay Active Metabolites from *Xenorhabdus spp.* Part 1. Dithiolopyrrolone Derivatives with Antibiotic Activity," *J. Nat. Prod.* 54:774–784 (1991) (copy enclosed).

Stachel et al., "Ring–Fused 1,2–Dithioles.1. Synthesis of Thiolutine and Related Compounds," *Liebigs Ann. Chem.* 473–480 (May, 1992).

Shiouaza et al., "Thiomarinol, a New Hybrid Antimicrobial Antibiotic Produced by a Marine Bacterium. Fermentation, Isolation, Structure and Antimicrobial Activity," *J. Antibiotics* 46:1834–1842 (1993).

Sharma et al., "Screening of Potential Chemopreventive Agents Using Biochemical Markers of Carcinogenesis," *Cancer Res.*, 15:5848–5855 (Nov. 15, 1994) (copy enclosed).

(List continued on next page.)

*Primary Examiner*—Fiona T. Powers (57) ABSTRACT

Compounds, isolated from the bacteria *Xenorhabdus bovienil*, have antineoplastic activity. The invention provides pharmaceutical compositions containing the compounds and the methods for employing them as medicaments, particularly in the treatment of human and animal cancers.

4 Claims, 1 Drawing Sheet

OTHER PUBLICATIONS

Chen, et al., "Antifungal Activity of 2 Xenorhabdus Species and Photorhabdus–Luminescens, Bacteria Associated with the Nematodes Steinernema Species and Heterorhabditis–Megidis," *Biological Control* 4:157–162 (1994).

Arnold et al., "Evaluation of Chemopreventive Agents in Different Mechanistic Classes Using a Rat Tracheal Epithelial Cell Culture Transformation Assay," *Cancer Res.* 55:537–543 (Feb. 1, 1995) (copy enclosed).

Li et al., "Antimicrobial Metabolites from a Bacterial Symbiont," *J. Nat. Prod.* 58:1081–1086 (Jul., 1995).

Shiouaza et al., "Thiomarinols B and C, New Antimicrobial Antibiotics Produced by a Marine Bacterium," *J. Antibiotics* 48:907–909 (Aug., 1995).

Li et al., "Identification of Two Pigments and a Hydroxystilbene Antibiotic from *Photorhabdus luminescens*," *Appl. Environ. Microbiol.* 61:4329–4333 (Dec., 1995).

Forst, et al., "Molecular Biology of the Symbiotic–Pathogenic Bacteria *Xenorhabdus spp.* and *Photorhabdus spp.*" Microbiol. Rev. 60:21–43 (Mar. 1996).

* cited by examiner

Figure 1 ion is a continuation-in-part of and claims
ANTINEOPLASTIC AGENTS

This application is a continuation-in-part of and claims the benefit of PCT/CA98/00841 filed Sep. 3, 1998, which is a continuation of application Ser. No. 08/921,851 filed Sep. 2, 1997, now abandoned, which is a continuation of application Ser. No. 08/627,589 filed Apr. 4, 1996, now abandoned, the disclosure of which is incorporated by reference.

FIELD OF THE INVENTION

The present invention relates to dithiolopyrrolone derivatives, their corresponding monoxides (xenomins) and dioxides (xenorxides) having antineoplastic activities. The present invention also provides antineoplastic compositions comprising these compounds, the salts thereof, and methods of using the inventive compounds as antineoplastic agents.

SUMMARY OF THE INVENTION

The present invention provides dithiolopyrrolone derivatives, their corresponding monoxides (xenomins) and dioxides (xenorxides) having antineoplastic activities. The present invention also provides antineoplastic compositions comprising these compounds, the salts thereof, and methods of using the inventive compounds as antineoplastic agents.

Compounds, xenorxides, isolated from the bacteria *Xenorhabdus bovienii*, have the formula in which $R_1$, $R_2$ hydrogen, substituted or unsubstituted alkyl, cycloally1, acyl, aryl, aralkyl, or heterocyclyl group; $R_3$=hydrogen, alkyl, cycloalcyl, arallyl or aryl group or the salt thereof. These compounds have antineoplastic activity. The invention provides processes for producing these compounds. The invention also provides pharmaceutical compositions containing the compounds and the methods for treatment employing them.

BRIEF DESCRIPTION OF THE DRAWINGS

The following

$R_1$=hydrogen, substituted or unsubstituted alkyl, cycloalkyl, aryl, aralkyl, or heterocyclic group; $R_2$=hydrogen, substituted or unsubstituted alkyl, cycloalkyl, aryl, aralkyl, heterocyclic or acyl group; $R_3$=hydrogen, alkyl, cycloalkyl, aralkyl, aryl or heterocyclic group.

BACKGROUND

Figure 1:
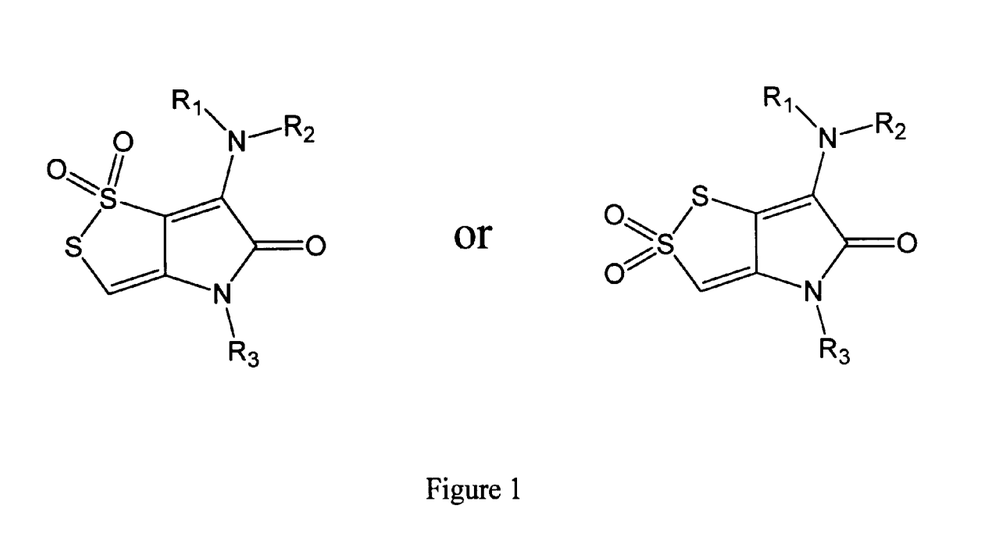
FIG. 1, represent the structural formula of dioxides (xenorxides) of dithiolopyrrolone.

Cancer is one of the major causes of death in humans and animals. Millions of people in the world are diagnosed every year as having cancer, and a large proportion of these people subsequently die of cancer. Although large effort has been made, cancers remain to be hard-to-treat diseases. There continues to be an urgent need for effective anticancer drugs. Soil organisms have been a traditional source of bioactive materials for the pharmaceutical and agrochemical industry. One of the recent developments has been the commercialization of a soil-living nematode-bacteria combination as biological control agents of insect pests. A crucial feature of this biocontrol agent is that the bacterial symbiont (Xenorhabdus spp. or Photorhabdus spp.) of the nematode produces a wide range of bioactive metabolites and some of these specific compounds have been isolated, identified and their structures elucidated (Forst and Nealson, 1996). Among these identified compounds, several are dithiolopyrrolone derivatives. Dithiolopyrrolones were initially isolated from Streptomyces in the nineteen-forties and have since then been isolated from other organisms. These compounds include aureothricin, thiolutin, holomycin and xenorhabdins (Hamao et al., 1948; Eisenman et al., 1953; Celmer and Solomons, 1955; yon Daehne et al., 1969; McInerney et al., 1991). These compounds possess antimicrobial activity against a wide range of micro-organisms. Recently, new antimicrobial substances, namely xenorxides (Webster et al., 1996), also were found from the bacterial cultures of Xenorhabdus spp. As a result of part of the ongoing exploration of the potential usefulness of these metabolites of Xenorhabdus, the xenorxides, xenomins and the dithiolopyrrolones have been found to be highly active against animal and human cancer cells, and is the subject of this invention.

Animal cells normally undergo various enzymatic and biochemical changes when influenced by various chemical factors. For example, when animal cells were challenged by carcinogens many enzymatic and biochemical -activities can be promoted and some of the promoted activities can be experimentally detected. Among dithiolopyrrolones and their derivatives, thiolutin is the one that has been studied extensively. Thiolutin inhibits RNA polymerase synthesis (Jimenez et al. 1973; Tipper. 1973) in yeast, has membrane stabilization activity and inhibit platelet aggregation (Yasuvuki et al., 1980) in rat. It has been reported (Menta and Moon. 1991; Shauma et al., 1994; Arnold et al., 1995) that thiolutin inhibited the promotion of several such activities that are possibly related to carcinogenesis in mammary cells that have been exposed to carcinogens. This suggested that thiolutin might be involved in the initiation of cell transformation or the progression of premalignant cells becoming malignant cancer cells. However, this activity has not experimentally established. Although the study of dithiolopyrrolones has been on-going for about 50 years. The anticancer activity of thiolutin and other dithiolopyrrolones against mammary cells has never been evaluated and reported until now. Xenorxides and xenomins have been discovered very recently, and there is no report in the prior art on their anticancer activity.

Although there are a limited number of publications on Xenorhabdus, it has been recognized that bioactive metabolites are produced by Xenorhabdus species. Some of these substances have been identified and their structures elucidated (Forst and Nealson, 1996, *Microbiol. Rev.* 60:21–43. Li et al., 1995, *J. Nat. Prod.* 58:1081–1085). Recently, the cell-free culture broths of Xenorhabdus species, bacterial symbionts carried by nematodes of the genus Steinernema, were found to be active against many fungi of agricultural and medicinal importance (Chen, G. et al., Biological Control 4:157–162.) Two new classes of antimicrobial substances, nematophin (Webster et al., U.S. patent application Ser. No. 08/412455, filed Mar. 29, 1995) and xenorxides (Webster et al., U.S. patent application Ser. No. 08/420307 filed Apr. 11, 1995), were found from these bacterial cultures. As a result of part of the ongoing exploration of the potential usefulness of these metabolites of Xenorhabdus, the xenorxides, have been found to be highly active against several human cancer cell lines, that is the subject of this invention.

DETAILED DESCRIPTION OF THE INVENTION

Although the compounds of the present invention may be synthesized chemically, the initial compounds were obtained from micro-organisms. The organisms used for this invention include *Xenorhabdus bovienii*, a symbiotic bacterium associated with entomopathogenic nematodes. *X. bovienii* and its nematode symbiont Steinernema feltiae, used in this invention, were collected from soil in British Columbia, Canada. Briefly, last instar larvae of the Greater Wax Moth, *Galleria mellonella*. were infected with infective juvenile (IJ) nematodes, carrying the *X. bovienii* A21 strain at a rate of 25 Us/larvae. After 24 to 48 h the dead insect larvae were surface disinfected by dipping them into 95% EtOH and igniting them. The cadavers were aseptically dissected, haemolymph was streaked onto an agar culture medium and incubated in the dark at room temperature. The agar medium has the following composition in one litre of distilled water:

| | |
|---|---|
| beef extract | 3 g |
| peptone | 5 g |
| bromothymol blue | 0.025 g |
| 2,3,5-triphenyltetrazolium | 0.04 g |
| Agar | 15 g |

Sterilized at 121° C. for 15 minutes.

The resulting primary form of *X. bovienii* was maintained and subcultured at 14 d intervals. For consistency, 14% sucrose lyophilized powder of the bacteria stored at −20° C. was frequently used as the starting material for cultures. Cultures of *X. bovienii* A21 strain from which the inventive compounds are obtained exhibit the characteristics listed in Table 1 and Table 2:

TABLE 1

Biochemical properties of *Xenorhabdus bovienii* A21 strain.

| | |
|---|---|
| Gram reaction | −* |
| Cell size (gm) | 5.3 × 2.2 |
| Mobility | + |
| Cell peritrichous | + |
| Pigmentation | yellow |
| Catalase | − |
| Oxidase | − |
| Urease | − |
| Lecithinase | + |
| Lipase (Tween 80) | + |

*+ positive; − negative.

TABLE 2

Acid production and utilization of carbon sources by *Xenorhabdus bovienii* A21 strain.

These characteristics are in agreement with those described for *X. bovienii* by Akhurst, R. J. and N. E. Boemare (1988), and, therefore, establishes the identity of the organism as *X. bovienii*. The bacterial strain from which the compounds of this invention were isolated was deposited under the Budapest Treaty in the American Type Culture Collection (ATCC), Rochville, Md. with a deposition number of ATCC 55743.

Cultivation of the microorganism *X. bovienii* yields bioactive substances, xenomins, xenorxides and dithiolopyrrolones. *X. bovienii* may be cultivated (fermented), for example, at about 25° C. under submerged aerobic conditions in an aqueous, nutrient medium containing assimilable carbon (carbohydrate) and nitrogen sources to obtain xenomins, xenorxides and dithiolopyrrolones. The fermentation may be carried out for a time period such as approximately 48 to 96 hours, at the end of which time these compounds have been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it is. The filtrate may then be extracted with a water immiscible, organic solvent, for example, with ethyl acetate or chloroform. The combined organic layers (e.g. pooled ethyl acetate or chloroform extracts) may be concentrated under vacuum (e.g., at about 30° C.) to an oily residue. The oily residue may be mixed with a small amount of organic solvent and chromatographed on a silica gel column. After introduction of the sample, chloroform or other organic solvent may be applied to elute the bioactive fraction. The bioactive fraction may be purified further by high performance, liquid chromatography (HPLC) with organic and/or aqueous solution.

In a conventional culture, the major compounds produced by *X. bovienii* are dithiolopyrrolones while xenorxides and xenomins are present in relatively small amounts. Alternatively, dithiolopyrrolones may be produced from other microorganisms, by chemical method(s) and/or a combination of both approaches.

The monoxides and dioxides of the corresponding dithiolopyrrolones isolated from *X. bovienii*, namely, xenorxides and xenomins, respectively may be transformed from their corresponding dithiolopyrrotone derivatives by biological or chemical means. By biological means, the culture broth of *X. bovienii*, with the corresponding dithiolopyrrotone derivatives present, may be filtered or centrifuged. The cell-free filtrate may be open to the air for extended periods from one week up to one month with or without stirring at room temperature or at other temperatures. This process may oxidize all or part of the corresponding dithiolopyrrotone derivatives to xenomins and xenorxides. Xenorxides and xenomins may be obtained by oxidation of the corresponding dithiolopyrrotone derivatives by chemical means. The pure dithiolopyrrotone derivatives or their mixture may be dissolved in a mixture of acetone and water, then oxidizing reagents such as potassium peroxymonosulfate and potassium bicarbonate may be added to the mixture. The mixture may be allowed to react for a period of several minutes up to more than one hour. The reaction mixture may be mixed with water, and extracted with organic solvent. The extracts may be combined, dried and purified by column chromatography or HPLC to obtain the corresponding xenorxides and/or xenomins. Additional monoxides and dioxides of the dithiolopyrrolones may be obtained from different microorganisms, synthesized chemically and/or produced by a combination of biological and chemical methods, and several examples are disclosed (Takahashi, et al., 1995; Fujimoto, et al. 1996).

The compounds of the present invention include dithiolopyrrolones, their corresponding monoxides such as xenomins, their corresponding dioxides such as xenorxides, and salts thereof. The term "salts", as used herein, denotes acidic and/or basic salts, formed with inorganic and/or organic acids and bases. Suitable acids include, for example, hydrochloric, sulfuric, nitric, benzenesulfonic, acetic, maleic, tartaric and the like which are pharmaceutically acceptable. It is well known to one skilled in the art that an appropriate salt is chosen based on physical and chemical stability, flowability, hydroscopicity and solubility. While pharmaceutically acceptable salts are preferred, particularly when employing the compounds of the invention as medicaments, other salts find utility, for example, in processing these compounds, or where non-medicament-type uses are contemplated. The antineoplastic agents and use thereof.

The present invention relates to pharmaceutical preparations which contain an active ingredient of these compounds or a pharmaceutically acceptable salt thereof. The dosage form and mode of administration as well as the dosage amount, may be selected by the skilled artisan. Exemplary daily dosages for an adult human are those within the range of about 2.5 mg to about 2,000 mg/day. Administration to a mammalian host may, for example, be oral, parenteral, or topical.

When these compounds or the salts thereof are used as therapeutics, they can be administered alone or in a pharmaceutically suitable formulation containing, in addition to the active ingredient, one or more conventional earners. Depending on the nature of the disease and/or route of administration, the composition of this invention can be formulated by known means.

Examples of pharmaceutical compositions include any solid (tablets, pills, capsules. granules, powder etc.) or liquid (solutions, suspensions or emulsions) compositions suitable for oral, topical or parenteral administration, and they may contain the pure compound or a salt thereof or in combination with any carrier or other pharmaceutically active compounds. These compositions may need to be sterile when administered parenterally.

The therapeutic compositions of the present invention being employed as antineoplastic agents for treatment of animal and human illness can be easily prepared in such unit dosage form with the employment of pharmaceutical materials which themselves are available in the art and can be prepared by established procedures. The appropriate solid or liquid vehicle or diluent nay be selected, and the compositions prepared, by methods known to the skilled artisan. The administration of any of the inventive compound and/or its pharmacologically active and physiologically compatible derivatives is useful for treating animals or humans having a neoplastic disease, for example, colon cancer, cevercal cancer, breast cancer, leukemia, lung cancer, ovarian cancer. CNS cancer, renal cancer, prostate cancer, etc. using the accepted protocols of the National Cancer Institute (NCI). The dosage administered will be dependent upon the identiy of the neoplastic disease. The type of host involved including its age, health and weight, the kind of concurrent treatment, if any, and the frequency of treatment and therapeutic ratio. Illustratively, dosage levels of the administered active ingredients are intravenous, 0.1 to about 200 mg/kg; intramuscular, 1 to about 500 mg/kg and orally, 5 to about 1000 mg/kg of host body weight. Expressed in terms of concentration, an active ingredient can be present in the compositions of the present invention for localized use in a concentration from about 0.01 to about 50% w/w of the composition, preferably about 1 to about 20% w/w of the composition, and for parenteral use in a concentration of from about 0.05 to about 50% w/v of the composition and preferably from about 5 to about 20% w/v. The active ingredients to be employed as antineoplastic agents, can be easily prepared in such unit dosage form with the employment of pharmaceutical materials which themselves are available in the art and can be prepared by established procedures.

The Microorganism

The bacterium, *Xenorhabdus bovienii* and its nematode symbiont, *Steinernema feltiae*, used in this study were collected from soil in British Columbia, Canada. The bacterial strain from which the compounds of this invention were isolated was deposited under the Budapest Treaty in the American Type Culture Collection, Rochville, Md. with a designation number of ATCC 55743. The procedure of isolation and the characteristics of this bacterial strain are fully described in Webster et al., U.S. patent application Ser. No. 08/420307 filed Apr. 11, 1995.

Production of Xenorxides

To prepare xenorxides, *X. bovienii* may be cultivated (fermented), for example, at about 25° C. under submerged aerobic conditions in an aqueous, nutrient medium containing assimilable carbon (carbohydrate) and nitrogen sources until xenorxides are imparted to the medium. The fermentation may be carried out for a time period such as approximately 48 to 96 hours, at the end of which time the xenorxides have been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it is. The filtrate may then be extracted with a water immiscible, organic solvent, for example, with ethyl acetate or chloroform. The combined organic layers (e.g. pooled ethyl acetate or chloroform extracts) may be concentrated in vacuum (e.g. about 30° C.) to an oily residue. The oily residue may be mixed with a small amount of organic solvent and chromatographed on a silica gel column. After introduction of the sample, chloroform or other organic solvent may be applied to elute the bioactive fraction. The bioactive fraction may be purified further by high performance, liquid chromatography (HPLC) with organic and/or aqueous solution.

Xenorxides are difficult to detect in the culture broth of *X bovienii*, but the corresponding dithiolopyrrolone derivatives are present in relatively large amounts. Alternatively, xenorxides may be transformed from their corresponding dithiolopyrrolone derivatives by biological or chemical means. By biological means, the culture broth of *X. bovienii*, with the corresponding dithiolopyrrolone derivatives present, may be filtered or centrifuged. The cell-free filtrate may be open to the air for extended periods from one week up to one month with or without stirring at room temperature or other temperatures. This process may oxidize all or part of the corresponding dithiolopyrrolone derivatives to xenorxides. Xenorxides may be obtained by oxidation of the corresponding dithiolopyrrolone derivatives by chemical means. The pure dithiolopyrrolone derivatives or their mixture may be dissolved in a mixture of acetone and water, then oxidizing reagents such as potassium peroxymonosulfate and potassium bicarbonate may be added to the mixture. The mixture may be allowed to react for a period of several minutes up to more than one hour. The reaction mixture may be mixed with water, and extracted with organic solvent. The extracts may be combined, dried and purified by column chromatography or HPLC to obtain the corresponding xenorxides.

The antineoplastic agents and use thereof.

Xenorxides have the chemical formula as shown below, wherein $R_1$, $R_2$=hydrogen, substituted or unsubstituted alkyl, cycloalkyl, acyl, aryl, aralykyl, or heterocyclyl croup; $R_3$=hydrogen, alkyl, cycloalkyl, aralkyl or aryl group. These compounds have strong antineoplastic activity ($IC_{50}$<0.1 μg/ml) against several human cancer cell lines. Most importantly, xenorxides inhibited the growth of cell lines HT29 human colon cancer ($IC_{50}$<0.1 μg/ml) as well as the growth of the cell line Hela cervical cancer and the cell line MCF-3 breast cancer ($IC_{100}$<1 μg/ml).

The present xenorxides form salts with acids when a basic functional group is present. All such salts are useful as pharmaceutically acceptable salts with acids. Suitable acids include, for example, hydrochloric, sulfuric, nitric, benzenesulfonic, acetic, maleic, tartaric and the like which are pharmaceutically acceptable.

The present invention provides methods of treating a mammal affected by tumors sensitive to compounds described above, which comprises administering to the affected individual a therapeutically effective amount of these compounds, the salts thereof or a pharmaceutical composition thereof. In particular, the compounds and the salts thereof of the invention may be used in treatment of mammalian colon, cevercal and breast cancer.

The present invention also relates to pharmaceutical preparations which contain an active ingredient of these compounds or a pharmaceutically acceptable salt thereof, as well as the process for its preparation.

Examples of pharmaceutical compositions include any solid (tablets, pills, capsules, granules, powder etc.) or liquid (solutions, suspensions or emulsions) in a suitable composition for oral, topical or parenteral administration, and they may contain the pure compound or in combination with any carrier or other pharmaceutically active compounds. These compositions may need to be sterile when administered parenterally.

The administration of xenorxides and its pharmacologically active and physiologically compatible derivatives is useful for treating animals or humans having a neoplastic disease, for example, colon cancer, cevercal cancer, breast cancer and the like using the accepted protocols of the National Cancer Institute. The dosage administered will be dependent upon the identity of the neoplastic disease; the type of host involved including its age, health and weight; the kind of concurrent treatment, if any; and the frequency of treatment and therapeutic ratio. Illustratively, dosage levels of the administered active ingredients are intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight. Expressed in terms of concentration, an active ingredient can be present in the compositions of the present invention for localized use about the cutis, intranasally, pharyngolaryngeally, bronchially, broncholially, intravaginally, rectally, or ocularly in a concentration from about 0.01 to about 50% w/w of the composition; preferably about 1 to about 20% w/w of the composition; and for parenteral use in a concentration of from about 0.05 to about 50% w/v of the composition and preferably from about 5 to about 20% w/v. The xenorxides, active ingredients to be employed as antineoplastic agents, can be easily prepared in such unit dosage form with the employment of pharmaceutical materials which themselves are available in the art and can be prepared by established procedures.

To further assist in the understanding of the present invention the following examples are presented to more clearly disclose the present invention and not by way of limitation.

EXAMPLE 1

Preparation of Xenorxides, Xenomins and the Dithiolopyrrolones

A. Preparation of Selected Dithiolopyrrolones.

Several dithiolopyrrolones have been reported so far, these include aureothricin, thiolutin, holomycin, xenorhabdins and thiomarinol. Aureothricin was initially reported by Umezawa et al. (1948), the structure were fully disclosed by Celmer and Solomons (1955). Thiolutin is produced by several bacterial species including *Streptoverticillium album*, which is available from the American Type Culture Collection(ATCC), Rockville, Md. with an ATCC number of 33049. The production of thiolutin and holomycin by chemical synthesis was published by Schmidt and Geiger (1962), Hagio, K. and Yonreda N. (1974) and Stachel, H. D., et al. (1992). Production of xenorhabdins was reported and fully reported by McInerney et al. (1991) and by Li et al.(1995). The preparation of additional different compounds with the dithiolopyrrolone ring was recently disclosed by Baggaley el al. (1994a, b) and by Takahashi et al. (1994). The dithiolopyrrolones used for the subject invention are prepared by the methods described in the cited references, and the structure of each dithiolopyrrolone derivative confirmed by its NMR spectroscopy. Skilled chemists will be able to use procedures as disclosed herein, and others, to obtain these dithiolopyrrolones from available stock substances. In carrying out such operations, any suitable filtration, chromatographic, and other purification techniques might be employed by those skilled in the art. It will be apparent to those skilled in the art that materials and reagents to carry out such operations are commercially available from chemical companies, so no details are given respecting them.

B. Preparation of the Corresponding Dioxides from Dithiolopyrrolones by Microbial Fermentation.

Xenorxides: Cultures of *X. bovienii* were shaken at 180 rpm on an Eberbach gyrorotary shaker for 24 h at 25° C. Bacterial fermentation was initiated by adding 100 ml of this bacterial culture to 900 ml of tryptic soy broth in a 2,000 ml flask. The flask was incubated in the dark at 25° C. on a gyrorotary shaker. After 96 h, the culture was immediately centrifuged (12,000 g, 20 minutes, 4° C.) to separate the bacterial cells. The cell-free broth was then extracted with ethyl acetate four times. The combined extracts were dried with anhydrous sodium sulfate and then filtered through filter paper. The filtrate was concentrated on a rotary evaporator below 30° C., under vacuum to yield a brown oil. After the above experiment was repeated 10 times, approximately 3 g of the oil was obtained. The crude extracts were then loaded onto a silica gel (200 g silica gel 60, 40 cm×5 cm, EM Science, Darmstadt. Germany) chromatographic column. The yellow bioactive fraction was eluted out with ether or ethyl acetate. This bioactive fraction was then subject to HPLC on a $C_{18}$ preparative column (Spherisorb 10 (ODS (1)), 250×10 mm. 10 micro, Phenomenex, Torrance, Calif.) with a progran (isocratic at 10% acetonitnile in water for 5 min, then gradually increasing to 85% acetonitrile in 35 min, isocratic for 5 min, then decreasing back to 10% in 2 min) at 2. 5 ml/min. The eluate was monitored at 254 nm. XENORXIDE 1 (about 0.3 mg per liter of the culture broth) was eluted at 33.6 min, and this was followed by XENORXIDE 2 (0.2 mg/l) which was eluted at 35.2 min.

C. Preparation of the Corresponding Monoxides from Dithiolopyrrolones by Microbial Fermentation Xenomins: For the purification of xenomins, the culture and extraction conditions were the same as for xenorxides. After the extraction, the concentrated crude extract was processed through a silica gel chromatographic column with ethyl acetate as the eluent. After the less polar bioactive material was eluted, the more polar bioactive fraction was obtained by eluting with methanol. The more polar bioactive fraction was concentrated under vacuum, and separated by a $C_1i$ chromatographic column first with water as eluent, then 25% methanol in water, 50% methanol, 75% methanol and finally, pure methanol. The most bioactive fraction was eluated with 75% methanol in water. This bioactive fraction was then concentrated and separated by HPLC on a Ct: preparative column (Spherisorb 10 (ODS(1)), 250×10 mm, 10 micro, Phenomenex, Torrance, Calif.) with a program (30% MeCN in $H_2O$ for 1 min and gradually increasing to 70% MeCN in $H_2O$ in 24 min, isocratic for 5 min) at 2.0 ml/min. The eluate was monitored at 254 nm. Active peak 1 (25.4 min) and peak 2 (25.8 min) were collected. Active peak 1 was concentrated, and further separated by preparative silica gel TLC with 60% ethyl acetate in dichloromethane as the eluent to give xenomin 1 ($R_f$=0.32). Active peak 2 was concentrated, and further separated by preparative silica gel TLC with 60% ethyl acetate in dichloromethane as the eluent to give xenomin 2 ($R_f$=0.31).

D. Preparation of Xenorxides from their Corresponding Dithiolopyrrolone Derivatives by Biological Transformation.

The cell-free broth was obtained using the same method as described above, and was then stored at 4° C. to room temperature for 3 to 6 weeks. Then the aqueous broth was extracted with ethyl acetate, and the combined extracts were separated using the same process discussed above. XENORXIDE 1 was eluted at 33.6 min (2 mg/l), XENORXIDE 2 was eluted at 35.2 min (1.5 mg/l).

E. Preparation of the Corresponding Dioxides from Dithiolopyrrolones by Chemical Oxidation.

One hundred and fifty two mg of 6-(hexanamido)-4-methyl-4,5-dihydro-1.2dithiolo[4,3-b]pyrrol-5-one (XNI) were dissolved in a mixture of 20 ml of acetone and 15 ml of water, and then cooled to 0° C. with ice. Potassium peroxymonosulfate (510 mg) was added to the solution at 0° C. The reaction mixture was stirred for one hour at 0° C. Then 5 ml of saturated solution of potassium bicarbonate was added to the reaction mixture with continuous stirring for 0.5 h at 0° C. The reaction mixture, after water was added, was extracted with ethyl acetate three times. The extracts were combined, dried over $Na_2SO_4$ and evaporated to give the crude product, which was then purified by silica gel column chromatography with hexane: ethyl acetate (2:1) to give pure xenorxide 1 (78 mg, 51% yield). Similarly, xenorxide 3 was produced from 6-(5'-methylhexanamido)4, 5dihydro-1,2-dithiolo[4,3-b]pyrrol-5one with 50% yield.

EXAMPLE 2

Identification of the Active Components

NMR spectra were recorded on a Bruker WM400 spectrometer in $CDCl_3$, using residual CDCl3 (−7.25) as internal standard. Low resolution mass spectra were obtained on a Hewlett-Packard 5985B GC/MS system operating at 70 eV using a direct probe. High resolution MS spectra were recorded on a Kratos MS80 instrument. IR spectra were recorded as neat film on NaCl using 8 Perkin-Elmer 599B spectrometer. (Abbreviations used as follows: EI=Electron Impact, M=Molecular Ion, t=triplet. J=coupling constant, Hz=Hertz, d=doublet, m=multiplet, bs=broad singlet).

6-(Acetamido)-4-methyl-4,5dihydro-1.2-dithiolo[4,3-b]pyrrol-5-one (Thiolutin) (XN0): $^1$HNMR (DMSO-$d_6$) δ 2.05 (3H, s), 3.92 (3H, s), 7.19 (1H, s) and 9.85 (1H, broad s); EIMS m/e 228 (M$^+$), 186.

6-(Hexanamido)-4-methyl-4,5-dihydro-1.2-dithiolo[4,3-b]pyrrol-5-one (XN1): $^1$HNMR (CDCl$_3$) δ 0.90 (3H, t, J=6.9 Hz), 1.35 (4H, m), 1.70 (2H, m), 2.35 (2H, t, J=7.4 Hz), 3.35 (3H, s), 6.63 (1H, s) and 7.43 (1H, broad s); EIMS m/e 284 (M$^+$), 186.

6(5'-Methylhexanamido)-4,5-dihydro1,2-dithiolo[4,3-b]pyrrol-5one (XN3): $^1$HNMR (CDCl$_3$) δ 0.89 (6H, d, J=6.6 Hz), 1.24 (3H, m), 1.70 (2H, m), 2.32 (2H, t, J=7.6 Hz), 6.74 (1H, s), 7.44 (1H, broad s) and 7.94 (1H, broad s); EIMS m/e 284 (M$^+$), 172.

XENORXIDE 1 (XO1): EIMS: 317 (2), 316 (M$^+$, 13), 220 (9), 219 (9), 218 (100), 186 154 (16), 99 (40), 71 (39); HRMS: 316.0555 (Calc. for $C_{12}H_{16}N_2O_4S_2$: 316.0551, 20), 217.9824 (Calc. for $C_6H_6N_2O_3S_2$: 217.9820, 100), 154.0197 (Calc. for $C_6H_6N_2OS$: 154.0201, 16); IR (KBr): 3448. 3298, 3275, 1720, 1686, 1654, 1637, 1560, 1522, 1310, 1139, 551 cm$^{-1}$; $^1$HN (CDCl$_3$) δ 7.56 (1H, bs, CO—NH), 6.35 (1H, s, H-3), 3.20 (3H, s, N—Me), 2.38 (2H, t, CO—CH$_2$, J=7.4 Hz), 1.67 (2H, m, CH$_2$), 1.32 (4H, m, CH$_2$CH$_2$), 0.89 (3H, t, J=7.0 Hz); $^{13}$CNMR (CDCl$_3$) δ 171.6 (s, CON), 164.7 (s, CO). 145.4 (s. C$_7$), 121.3 (s, C$_6$), 116.2 s, C$_8$), 109.2 d, C$_3$), 36.4, 31.2, 27.8, 24.6, 22.3, 13.8.

XENORXIDE 2 XO2); EIMS: 330 M$^+$, 10), 218 (100); HRMS: 330.0707 Calc. for $C_{13}H_{18}N_2O_4S_2$: 330.0708, 18), 217.9829 Calc. for $C_6H_6N_2O_3S_2$: 217.9820. 100), 154.0213 (Calc. for $C_6H_6N_2OS$ 154.0201, 16). IR (KBr): 3438, 3298, 1719, 1686, 1654, 1637, 1560, 1522, 1400, 1310, 1142, 551 cm$^{-1}$; $^1$HNMR (CDCl$_3$) δ 7.56 (1H, bs, CO—NH), 6 35 (1H, s, H-3), 3.20 (3H, s, N—Me), 2.36 (2H, t, CO—CH$_2$, J=7.4 Hz), 1.67 (2H, m, CH$_2$), 1.2–1.6 (1H, m, CH), 1.22 (2H, m, CH$_2$), 0.89 (6H, d, J=6.6Hz); Different NOE experiment showed the NOE effect between the peak at 6.35 ppm and 3.20 ppm; $^{13}$CNMR (CDCl$_3$) δ 171.6 s, CON), 164.7 s, CO), 145.4 (s, C$_7$), 121.3 s, C$_6$), 116.2 s, C$_8$), 109.2 d, C$_3$), 38.2 t, CH$_2$), 36.7(t, CH$_2$), 28.0 q, CH$_3$), 27.8 d, CH), 22.8 t, CH$_2$, 22.4 q, CH$_3$).

XENORXIDE 3 XO3): EIMS: 316 M$^+$, 7.5), 218 (9), 204 (65) 185 (7), 172 (15), 105 (25), 95 (95), 69 (100), 43 (70);

¹HNMR (CDCl₃) δ 10.10 (1H, bs), 9.32 (1H, bs), 6.85 (1H, s, H-3), 2.53 (2H, t, CO—CH₂, J7.5 Hz), 1.66 (2H, m, CH₂), 1.58 (1H, m), 1.21 (2H, m, ), 0.87 6H, d, J=6.6 Hz).

Xenomin 1 XM1): EIMS: 300 (M⁺, 13), 202 (36), 186 (44), 185 (41), 85 (62), 69(100); HRMS: 300.0605 (Calc. for C₁₂HR₁₆N₂O₃S₂: 300.0602, 12), 201.9871 Calc. for C₆H₆N₂O₂S₂201.9871, 30); ¹HNMR (CDCl₃) d: 7.52 (1H, bs,CO—NH), 6.46 (¹H, s, H-3), 3.30 (3H, s, N-Me), 2.49 (2H, t, CO—CH₂, J=7.4 Hz), 1.79 (2H, m, CH₂), 1.41 (4H, m, CH₂–CH₂), 0.90 (3H, t, J=6.9).

Xenomin 2 XM2): EIMS: 314 M⁺, 21), 218 (15), 202 (59), 187 (18), 186 (98), 185 (73), 69 (100): HRMS: 314.0759 Calc. for C₁₃H₁₈N₂O₃S₂: 314.0759, 12), 201.9871 Calc. for C₆H₆N₂O₂S₂: 201.9871, 45); ¹HNMR (CDCl₃) d: 7.43 (1H, bs, CO—NH), 6.46 (¹H, s, H-3), 3.30 (3H, s, N-Me), 2.48 (2H, t, CO—CH₂, J=7.6 Hz), 1.71 (2H, m, CH₂), 1.29 (3H, m, CH and CH₂), 0.88 (6H, d, j=7.0). Example 3. Dithiolopyrrolones, the corresponding monoxides and dioxides as antineoplastic agents.

The anticancer activity of a particular compound can be demonstrated by standard assays. The method normally used by the American National Cancer Institute (NCI) for the effectiveness of a compound is based on the $LC_{50}$. The $LC_{50}$ is the compound concentration at which half of the cancer cell population is killed. The assay is commonly used by those skilled in the art and are accepted as indicative of anticancer activity in mammals. The test animal cancer cells are available from ATCC, NCI and other organizations. The anticancer activities of compounds of the present invention have been determined in cell cultures of various human cancer cells (see table below) using the standard NCI method with slight modifications. The specifications of the procedure was described by Skehan et al. (1990). Briefly, cancer cells were grown in RPMI-1640 medium with glutamine and 10% fetal calf serum, and were harvested from exponential-phase maintenance cultures. The harvested cells were counted and dispensed into replicate 96-well culture plates in 180 μl volumes for each well with a cell density of up to 2,500 cells/well. The cells were allowed to settle for about 4 hours at 37° C. Then 20 μl of medium containing the test compound was added into each well, resulting in a suitable final test compound concentration. The test plates were then incubated at 37° C. The test was terminated after incubation by adding to each well 50 1 of cold 50% trichloroacetic acid. The cells were fixed for an hour at 4° C. and then washed five times with tap water. The washed plates were air-dried and stained for 30 minutes with 0.4% (wt/vol) sulforhodamine B (SRB) which was dissolved in 1% acetic acid. At the end of the staining period, the SRB was removed and plates were quickly rinsed five times with 1% acetic acid. After being rinsed, the plates were air-dried and 100 μl of 10 mM tris base (pH 10.5) were added to each well to dissolve the dye bound to the cells. The plates were placed on a gyratory shaker and shaken (100 rpm) for 10 minutes. Finally, the plates were read in a microtiter plate reader at 570 nm. All the compounds tested exhibited very strong anticancer activity against these cancer cells (see table below).

Antitneoplastic activity:

| Cancer cells | $LC_{50}$ ($10^{-6}$ M) | | | | | | |
|---|---|---|---|---|---|---|---|
| | XN0 | XN1 | XN3 | XO1 | XO2 | XM1 | XM2 |
| HT29 | 0.13 | 0.11 | 0.11 | 0.22 | 0.85 | 0.47 | 0.11 |
| MCF-7 | 0.35 | 0.56 | 0.39 | 0.89 | 0.95 | 0.47 | 0.55 |
| Hela | 0.31 | 0.46 | 0.32 | 0.16 | 0.13 | 0.80 | 0.21 |
| P388 | —* | — | — | 0.66 | 0.28 | — | — |
| NCI-H460 | — | — | 0.03 | 0.28 | 0.22 | — | — |
| Sk-Mel-28 | — | — | 0.24 | 0.19 | 0.73 | — | — |
| LNCap | — | — | — | 0.54 | 0.19 | — | — |
| DU-145 (Prostate cancer) | — | — | 0.14 | 1.80 | 1.60 | — | — |
| UO-31 (Renal cancer) | — | — | 0.18 | 1.85 | 6.0 | — | — |
| SF-295 (CNS cancer) | — | — | 0.04 | 1.58 | 2.12 | — | — |

*not tested.

From the foregoing embodiments and examples, it is apparent that an invention has been herein described and illustrated. While our above description contains many specificities, these should not be construed as limitations on the scope of the invention, but rather as examples of preferred embodiments. Accordingly, the scope of the invention should not be determined by the embodiments presented, but by the appended claims and their legal equivalents.

EXAMPLE 3

Isolation of Xenorxides from the Culture Broth of *X. bovienii*

Cultures were shaken at 180 rpm on an Eberbach gyrorotary shaker for 24 h at 25° C. Bacterial fermentation was initiated by adding 100 ml of this bacterial culture to 900 ml of trptic soy broth in a 2,000 ml flask. The flask was incubated in the dark at 25° C. on a gyrorotary shaker. After 96 h, the culture was immediately centrifuged (12,000 g, 20 minutes, 4° C.) to separate the bacterial cells. The cell-free broth was then extracted with ethyl acetate 4 times. The combined extracts were dried with anhydrous sodium sulfate and then filtered through filter paper. The filtrate was concentrated on a rotary evaporator below. 30° C., under vacuum to yield a brown oil. After the above experiment was repeated 10 times, approximately 3 g of the oil was obtained. The crude extracts were then loaded onto a silica gel (200 g silica gel 60, 40 cm×5 cm, EM Science, Darmstadt, Germany) chromatographic column. The yellow bioactive fraction was eluted out with ether or ethyl acetate. This bioactive fraction was then subject to HPLC on a $C_{18}$ preparative column (Spherisorb 10 ODS(1)), 250×10 mm, 10 micro, Phenomenex, Torrance, Calif.) with a program (isocratic at 10% acetonitrile in water for 5 min, then gradually increasing to 85% acetonitrile in 35 min, isocratic for 5 min, then decreasing back to 10% in 2 min) at 2.5 ml/min. The eluate was monitored at 254 nm. XENORXIDE 1 (about 0.3 mg per liter of the culture broth) was eluted at 33.6 min, and XENORXIDE 2 (0.2 mg/l) was eluted at 35.2 min.

EXAMPLE 4

Preparation of Xenorxides from their Corresponding Dithiolopyrrolone Derivatives by Biological Transformation The cell-free broth was obtained using the same method as described above, and was then stored a 4° C. to room temperature for 3 to 6 weeks. Then the aqueous broth was extracted with ethyl acetate, and the combined extracts were separated using the same process discussed above. XENORXIDE 1 was eluted at 33.6 min (2 mg/l), XENORXIDE 2 was eluted at 35.2 min (1.5 mg/l).

EXAMPLE 5

Preparation of Xenorxides by Chemical Oxidation

One hundred and fifty two mg of 6-(1 exanamido)4-methyl4,5-dihydro-1,2-dithiolo[4,3-b]pyrrol-5-one were dissolved in a mixture of 20 ml of acetone and 15 ml of water, and then cooled to 0° C. with ice. Potassium peroxymonosulfate (510 mg,) was added to the solution at 0° C. The reaction mixture was stirred for one hour at 0° C. Then 5 ml of saturated solution of potassium bicarbonate was added to the reaction mixture with continuous stirring for 0.5 h at 0° C. The reaction mixture, after water was added, was extracted with ethyl acetate three times. The extracts were combined, dried over $Na_2SO_4$ and evaporated to give the crude product, which was then purified by silica gel column chromatography with hexane: ethyl acetate (2:1) to give pure xenorxide 2 (78 mg, 51% yield). Similarly, xenorxide 3 was produced from 6-(5'-methylhexanamido)4,5-dihydro-1,2-dithiolo[4,3-b]pyrrol-5one with 50% yield.

EXAMPLE 6

Identification of the Active Components Form *X. bovienii*

NMR spectra were recorded on a Bruker WM400 spectrometer in CDCl3 using residual CDCl3 (−7.25) as internal standard. Low resolution mass spectra were obtained on a Hewlett-Packard 5985B GC/MS system operating at 70 eV using a direct probe. High resolution MS spectra were recorded on a Kratos MS80 instrument. IR spectra were recorded as neat film on NaCl using a Perkin-Elmer 599B spectrometer. (Abbreviations used as follows: EI=Electron Impact, M=Molecular Ion, t triplet, J=coupling constant, Hz=Hertz, d=doublet, m=multiplet, bs=broad singlet).

XENORXIDE 1: EIMS: 330 ($M^+$, 10), 218 (100); hrms: 330.0707 (Calc. for $C_{13}H_{18}N_2O_4S_2$: 330.0708, 18), 217.9829 (Calc. for $C_6H_6N_2O_3S_2$: 217.9820, 100), 154.0213 (Calc. for $C_6H_6N_2OS$: 154.0201, 16); IR (KBr): 3438, 3298, 1719, 1686, 1654, 1637, 1560, 1522, 1400, 1310, 1142, 551 $cm^{-1}$; $^1$HNMR ($CDCL_3$) δ: 7.56 (1H, bs,CO—NH), 6.35 (1H, s, H-3), 3.20 (3H, s, N-Me), 2.36 (2H, t, CO—CH2, J=7.4 Hz), 1.67 (2H, m, CH2), 1.2–1.6 (1H, m, CH), 1.22 (2H, m, $CH_2$), 0.89 (6H, d, J=6.6Hz); Different NOE experiment showed the NOE effect between the peak at 6.35 ppm and 3.20 ppm; $^{13}$CNMR ($CDCL_3$), δ: 171.6 (s, CON), 164.7 (s,CO), 145.4 s, $C_7$), 121.3 (s, $C_6$), 116.2 (s, $C_8$), 109.2 (d, $C_3$), 38.2 (t, $CH_2$), 36.7 (t, $CH_2$), 28.0 (q, $CH_3$), 27.8 (d, CH), 22.8 (t, $CH_2$), 22.4 (q, $CH_3$).

XENORXIDE 2: EIMS: 317 (2), 316 ($M^+$, 13), 220 (9), 219 (9), 218 (100), 186 (23), 154 (16), 99 (40), 71 (39); HRMS: 316.0555 Calc. for $C_{12}H_{16}N_2O_4S_2$: 316.0551, 20), 217.9824 (Calc. for $C_6H_6N_2O_3S_2$: 217.9820, 100), 154.0197 (Calc. for $C_6H_6N_2OS$: 154.0201, 16) IR (KBr): 3448, 3298, 3275, 1720, 1686. 1654, 1637, 1560, 1522, 1310, 1139, 551 $cm^{-1}$; $^1$HNMR ($CDCl_3$) δ: 7.56 (1H, bs,CO—NH), 6.35 (1H, s, H-3), 3.20 (3H, s, N-Me), 2.38 (2H, t, CO—$CH_2$, J=7.4Hz), 1.67 (2H, m, $CH_2$), 1.32 (4H, m, $CH_2CH_2$), 0.89 (31H, t, J=7.0 Hz); $^{13}$CNMR (CDCL) δ: 171.6 (s, CON), 164.7 s, CO), 145.4 (s, $C_7$), 121.3 (s, $C_6$), 116.2 (s, $C_8$), 109.2 (d, $C_3$), 36.4, 31.2, 27.8, 24.6, 22.3, 13.8.

XENORXIDE 3: EIMS: 316 ($M^+$, 7.5), 218 (9), 204 (65) 185 (7), 172 (15), 105 (25), 95 (95), 69 (100), 43 (70); $^1$HNMR ($CDCl_3$) δ: 10.10 (1H, bs), 9.32 (1H, bs), 6.85 (1H, s, H-3), 2.53 (2H, t, CO—$CH_2$, J=7.5 Hz), 1.66 (2H, m, $CH_2$), 1.58 (1H, m), 1.21 (2H, m,), 0.87 (6H, d, J=6.6 Hz).

EXAMPLE 7

Xenorxides as Antineoplastic Agents

The antineoplastic activities of xenorxides have been determined 'in vitro' in cell cultures of human colon cancer cell line HT29, breast cancer cell line MCF-3 and cervical cancer cell line Hela. The procedure was carried out using the method described by R. J. Bergeron et al., 1984. Biochem.Bioph. Res. Comm. 121:845–854, by A. C. Shroeder et al., 1981. J.Med. Chem. 24:1078–1083 and by Monks et al., 1991. J. Natl. Cancer Inst. 83:757–766.

| | Antineoplastic activity: | | |
|---|---|---|---|
| | | $IC_{50}$ (μg/ml) | |
| Compound | HT29 | MCF-3 | Hela |
| Xenorxide 1 | <0.1 | <0.1 | <0.1 |
| Xenorxide 2 | <0.1 | <0.1 | <0.1 |

EXAMPLE 8

Anticancer Activity of Xenorxide Derivatives Against Human Lung Cancer (H460) and Breast Cancer (LCC6)

| | | | | IC50 | |
|---|---|---|---|---|---|
| Code | Structure | Formulate | FW | H460 | LCC6 |
| CSL-29 |  | $C_{19}H_{14}N_2O_4S_2$ | 398 | 1.98 | 1.97 |

-continued

| Code | Structure | Formulate | FW | IC50 H460 | LCC6 |
|---|---|---|---|---|---|
| CSL-30 | | $C_{17}H_{10}N_2O_4S_2$ | 322 | 0.56 | 0.67 |
| BLI-041-1 | | $C_{14}H_9N_2O_5F_3S2$ | 406 | 2.13 | 6.38 |
| BLI-042-1 | | $C_{14}H_{12}N_2O_5S_2$ | 352 | 0.23 | 1.63 |

Structures and parameters of Xenorxides derivatives:

1. CSL-29
   $R^1$=Bz; $R_2$=Ph; $R_3$=H.
   $^1$H NMR(100 MHz, CDCl$_3$) δ2.3 s, 3H). 6.4 s, 1H), 7.2–7.6 (mullet, 5H), 7.7 s, 1H).
2. CSL-30
   $R^1$=Ph; $R_2$=CH$_3$; $R_3$=H
   $^1$H NMR(100 MHz, CDCl$_3$) δ4.8 (s, 2H), 6.2 s, 1H), 7.2–8.0 (mullet, 10H), 8.3 (s, 1H).
3. BLI-042
   $R_1$=—C$_6$H$_4$OCH$_3$ (4-methoxy-phenyl); $R_2$=CH$_3$; $R_3$=H.
   $^1$H NMR(100 z, CDCl$_3$) δ2.1 (s, 3H), 3.9 (s, 3H), 6.4(s, 1H), 6.9–7.4 (dd, 4H), 7.8 (s, 1H).
4. BLI-061
   $R_1$=Bz;$R_2$=CH$_3$; $R_3$=H.
   $^1$H NMR(100 MHz, CDCl$_3$) δ2.2 s, 3H), 5.0 s, 2H), 6.4 (s, 1H), 7.2 s, 5H), 8.1 s, 1H).

EXAMPLE 9

Synthesis of Xenorxide Derivatives

Xenorxides can be prepared from dithiolopyrrolones by oxiding the corresponding dithiolopyirolone derivatives as shown below:

To a solution of xenorhabdin (0.2 mmol) in 20 ml acetone a solution of XONE(0.8 mmol) in water was added and the resulted solution was stirred for 4 hours. It was extracted with ethyl acetate and the extracting solution was dried on MgSO$_4$ and evaporated under reduced pressure. Residual was cbromatographied in a column of silica gel to give Xenorxide in about 50% yield. REFERENCES CITED
1. Akhurst, R. J. and N. E. Boemare, 1988. J Gen. Microbiol. Vol. 134, 1835–1845
2. Arnold, J. T. et al., 1995. Cancer Research 55:537–543.
3. Baggaley, K. H. et al., 1994a. WO 94/26750.
4. Baggaley, K. H. et al., 1994b. WO 94/28001.
5. Celmer, W. D. and I. A. Solomons 1955. J. Amer. Chem. Soc. 77:2861–2865.
6. Eisenan, W. et al., 1953. Antibiotics and Chemotherapy 3: 385–392.
7. Forst, S. and K. IvTealson, 1996. Microbiol. Rev. 60:21–43.
8. Fujimoto, K. et al., 1996. WO 96/23795.
9. Hagio, K. and Yoneda, N. 1974. Bull. Chem. Soc. Japan. 47:1484–1489.
10. Jimenez. A. et al. 1973. Antimicrob. Ag. Chemother. 729–738.
11. Li. et al., 1995. 4ppl. Environ. Microbiol. 61:4329–4333.
12. Li. J. et al., 1995. J. Nat. Prod. 58:1081–1085.
13. McInerney, B. V. et al., 1991. J. 'Vat. Prod. 54:774–784.
14. Menta R. G, and R. C. Moon, 1991. Anticancer Research 11:593–596.
15. Monks et al., 1991. J. Natl. Cancer Inst. 83:757–766.
16. Ninomiya, Y. T. et al., 1980. Chem. Pharm. Bull. 28:3157–3162.
17. Sharma, S. et al., 1994. Cancer Research 54:5848–5855.
18. Shroeder et al. 1981. J. Med. Chem. 24:1078–1083.
19. Skehan, P. et al. 1990. J. Natl. Cancer Inst 82:1107–1118.
20. Stachel, H. D. et al. 1992. Liebigs Ann. Chem. 473–480.
21. Takahashi S. et al. 1994. U.S. Pat. No. 5,292,892.
22. Takahashi S. et al. 1995. U.S. Pat. No. 5,399,711.
23. Tipper D. J. 1973. J. Bacteriol. 116:245–256.
24. Umezawa, H. et al. 1948. Jap. Med. J. 1:512–517.
25. Webster et al. WO: 96/32396.
26. von Daehne, W. et al., 1969. 7. Antibiotics 22:233–235.

We claim:

1. A method of inhibiting the growth of mammalian tumors, comprising administering to a subject in need of such treatment, an effective antineoplastic amount of a compound of the structure shown below,

A

-continued

B wherein $R_1$, $R_2$=hydrogen, substituted or unsubstituted alkyl, cycloalkyl, acyl, aryl, aralkyl, or heterocyclic group; $R_3$=hydrogen, alkyl, cycloalkyl, aralkyl, aryl or heteocyclic group or a pharmaceutically acceptable salt thereof in association with a pharmaceutical carrier or dilution.

2. A method of inhibiting the growth of mammalian tumors, comprising administering to a subject in need of such treatment, an effective amount of a compound of claim 1, wherein $R_1$=hydrogen, substituted or unsubstituted alkyl, cycloalkyl, aryl, aralkyl, or heterocyclic group; $R_2$acyl; $R_3$=hydrogen, alkyl, cycloalkyl, aralkyl, aryl or heteocyclic group, or a pharmaceutically acceptable salt thereof, in association with a pharmaceutical carrier or dilution.

3. A method of inhibiting the growth of mammalian tumors, comprising administering to a subject in need of such treatment, an effective amount of a compound of claim 1, wherein $R_1$=hydrogen; $R_2$=acyl; $R_3$ hydrogen, methyl; or a pharmaceutically acceptable salt thereof, in association with a pharmaceutical carrier or dilution.

4. A method of inhibiting the growth of mammalian tumors, comprising administering to a subject in need of such treatment, an effective amount of a compound of claim 1, wherein $R_1$=hydrogen; $R_2$=acyl group with a straight or branched one to ten carbon chain; $R_3$=hydrogen, or methyl or a pharmaceutically acceptable salt thereof, in association with a pharmaceutical carrier or dilution.

* * * * *